United States Patent [19]

Ellis, Jr. et al.

[11] Patent Number: 4,900,871
[45] Date of Patent: Feb. 13, 1990

[54] HYDROCARBON OXIDATIONS CATALYZED BY IRON COORDINATION COMPLEXES CONTAINING A HALOGENATED LIGAND

[75] Inventors: Paul E. Ellis, Jr., Downingtown; James E. Lyons, Wallingford; Harry K. Myers, Jr., Cochranville, all of Pa.

[73] Assignee: Sun Refining and Marketing Company, Philadelphia, Pa.

[21] Appl. No.: 66,666

[22] Filed: Jun. 26, 1987

Related U.S. Application Data

[63] Continuation-in-part of Ser. No. 246, Jan. 2, 1987.

[51] Int. Cl.$^4$ .................. C07C 45/32; C07C 45/33
[52] U.S. Cl. .................... 568/399; 260/413; 260/410.9 R; 560/241; 568/398; 568/910; 568/910.5; 562/512; 562/549
[58] Field of Search ............... 562/549, 512.2; 568/399, 398.8, 910, 910.5; 560/241, 241.1; 260/413, 410.9 R

[56] References Cited

U.S. PATENT DOCUMENTS

| | | | |
|---|---|---|---|
| 3,816,548 | 6/1974 | Williams et al. | 568/399 X |
| 3,873,625 | 3/1975 | Barone | 568/399 X |
| 4,028,423 | 6/1977 | Brownstein | 568/399 X |
| 4,459,427 | 7/1984 | Middleton et al. | 568/910 X |

Primary Examiner—Werren B. Lone
Attorney, Agent, or Firm—J. Edward Hess; Donald R. Johnson

[57] ABSTRACT

Hydrocarbons, and particularly lower molecular weight alkanes and cycloalkanes, may readily be oxidized with air or $O_2$ to form such products as alcohols, ketones, and the like selectively high yields when there is employed as the catalyst a coordination complex containing an iron center and a halogenated ligand having the structure

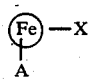

where Fe is iron; "O" is a ligand; X is a halogen substituent of the ligand; and A is an anion.

8 Claims, No Drawings

HYDROCARBON OXIDATIONS CATALYZED BY IRON COORDINATION COMPLEXES CONTAINING A HALOGENATED LIGAND

This application is a continuation-in-part of U.S. application Ser. No. 246, filed Jan. 2, 1987 in the name of Paul E. Ellis, Jr., James E. Lyons, and Harry K. Myers, Jr.

BACKGROUND OF THE INVENTION

This invention relates to a novel process for the oxidation of hydrocarbons. More particularly, this invention relates to the catalytic oxidation of a wide range of oxidizable hydrocarbons, particularly alkanes, with air or oxygen. The catalyst is a halogenated ligand complex of compounds containing one or more cations of iron.

The oxidation of alkanes and other aliphatic hydrocarbons catalyzed by transition metal complexes in the liquid phase is well known in the art, and commercial applications of this technology are extensive. See, for example, J. E. Lyons, *Hydrocarbon Processing*, November, 1980, 107, Table I.

However, the selective partial oxidation of unactivated hydrocarbons such as methane, ethane, propane, butanes and the like by air or oxygen as the oxidant is extremely difficult to achieve. The use of macrocyclic metal complexes such as metalloporphyrins as catalysts in the liquid phase has not been successful in giving rapid rates and high selectivities under mild conditions using air or oxgen as the oxidant. Some success has been achieved using two less economically desirable approaches:

(1) The use of metalloporphyrin catalysts such as Fe(TPP)Cl and Mn(TPP)Cl (where "TPP" is the dianion of 5, 10, 15, 20-tetraphenylporphine) with iodosylbenzene, sodium hypochlorite, alkylhydroperoxides or other expensive non-regenerable oxidants. [P. Traylor, D. Dolphin, and T. Traylor, *J. Chem. Soc. Chem. Comm.*, 279 (1984); J. Groves, W. Kruper, Jr., and R. Haushalter, *J. Am. Chem. Soc.*, 102, 6377 (1980); C. Hill, and B. Schardt, *J. Am. Chem. Soc.*, 102, 6374 (1980); J. Smegal and C. Hill, *J. Am. Chem. Soc.*, 105, 3515 (1983); A. Middleton and D. Smith, U.S. Pat. No. 4,459,427 (July 10, 1984)]; and (2) The use of metalloporphyrin catalysts with molecular oxygen as oxidant and simultaneous addition of a reductant such as $NaBH_4$, ascorbic acid or colloidal platinum with $H_2$. Again, the added reagents are expensive and non-regenerable. Examples of this approach can be found in D. Mansuy, M. Fontecave, and J. Bartoli, *J. Chem. Soc. Chem. Comm.* 253 (1983); I, Tabushi and A. Yazaki, *J. Am. Chem. Soc.*, 103, 7371 (1981).

It is, therefore, an object of this invention to provide an improved metal coordination complex-catalyzed process for the oxidation of hydrocarbons, and particularly alkanes, using air or oxygen, but without the need for added expensive, non-regenerable oxidants, reductants, or other co-catalysts.

SUMMARY OF THE INVENTION

In accordance with the present invention, it has now been found that hydrocarbons generally, and alkanes in particular, desirably those hydrocarbons having from about 1 to 20 carbon atoms, and preferably those having from 1 to 10 carbon atoms, may readily be oxidized with air to selectively form the corresponding hydrocarbon oxidation products such as alcohols and ketones with minor amounts of esters, acids and the like, when the catalyst is a halogenated coordination complex containing one or more iron cations, as defined below. More particularly, it has been found that halogenating the ligand systems of these iron cation-containing coordination complexes can convert a complex which is otherwise catalytically inactive, or has low catalytic activity, into a highly active catalyst for the selective oxidation of difficult-to-oxidize alkanes to form alcohols, ketones, or mixtures thereof, in good yield with little formation of the undesirable carbon oxides.

The use of these catalysts in the oxidation of hydrocarbons, and especially alkanes, results in several unexpected advantages. As in the pending application of Ellis, et al, disclosing azide-activated ligand complexes of transition metals (S.N. 246), the reaction can be carried out as lower temperatures than heretofore employed; there is often little or no cleavage of the starting material; there is little or no formation of CO or $CO_2$; there is higher selectivity for alcohols, when alcohols are the desired product; the reaction rates are generally faster than those of comparable prior art processes; and the processes themselves are less expensive than those of the prior art which require strong oxidants. However, in addition, the specific use of the iron cation and the halogenated ligand in the catalyst coordination complex results in surprisingly higher catalyst activity and even higher selectivity for alcohols, when alcohols are the desired product, than are found with other transition metal cations or with unhalogenated iron coordination complexes.

DESCRIPTION OF THE INVENTION

The process of this invention, which is applicable to hydrocarbons of any carbon atom content, is particularly applicable to alkanes, which are known to be more difficult to oxidize than other types of hydrocarbons. However, it will be understood that the aforesaid catalysts are also very effective in the oxidation of other classes of hydrocarbons as well, especially those containing substituents which will enhance the reactivity of the carbon-hydrogen bond with oxygen, i.e. "activated hydrocarbons", as described below.

As aforestated, this process is particularly effective in the oxidation of alkanes, including cycloalkanes, substituted alkanes and the like. The alkane starting materials thus include straight and branched-chain compounds having from about 1 to 20 carbon atoms, preferably 1 to 10 carbon atoms, such as methane, ethane, propane, n-butane, isobutane, n-pentane, n-hexane, 2-methylpentane, 3-methylpentane, heptane, 2-methylheptane, 3-methylheptane and the like, as well as cycloalkanes having from about 5 to 20 carbon atoms, preferably 5 to 10 carbon atoms, such as cyclopentane, cyclohexane, cycloheptane, cyclooctane, and the like. These compounds, if desired, may be substituted with various moieties, although care should be taken to exclude substituents which will adversely affect the activity of the catalyst.

When the foregoing alkanes are oxidized in accordance with the process of this invention, the corresponding alcohols, ketones, and the like are obtained. Thus, this process is generally applicable to the preparation of a broad class of known materials which may be used, for example, as solvents, chemical intermediates, commodity chemicals, polymer intermediates, gasoline additives, and the like.

Illustrations of activated hydrocarbons which may also be oxidized by the process of this invention include such compounds as toluene, xylenes, cumene, ethylbenzene, diphenylmethane, fluorene, and like alkyl-substituted aromatics having from about 7 to 20 carbon atoms, preferably 7 to 12 carbon atoms. Also included are olefinic hydrocarbons, particularly those containing allylic carbon-hydrogen bonds, as, for example, propylene, butenes, cyclohexene, and the like. In addition, the catalysts of this process are able, in many instances, to oxidize olefinic double bonds directly to give epoxides, ketones and alcohols, which are also useful as solvents, chemical intermediates, and the like. The olefins desirably have from about 2 to 20 carbon atoms, preferably 2 to 8 carbon atoms.

Finally, the process of this invention is also applicable to the further oxidation of partially oxidized hydrocarbons other than, of course, organic acids. Generally these partially oxidized hydrocarbons have from about 1 to 20 carbon atoms, that is, they are similar to the hydrocarbons as described above except for being partially oxidized.

The foregoing description of the starting materials shows that this process is widely applicable to a broad range of oxidizable hydrocarbons, of which the oxidation of alkanes represents a preferred embodiment of this invention. As stated above, these hydrocarbons may contain various substituents as long as they do not adversely affect the activity of the catalyst.

The oxidation, which may be carried out in a generally known manner, is desirably conducted in the liquid phase, although this is not critical, using such organic solvents as benzene, acetic acid, acetonitrile, methyl acetate, or like solvents which are inert to the conditions of the reactions, or in a neat solution of the hydrocarbon if it is liquid, and under pressures ranging from about 15 to 1500 psig, preferably 30 to 750 psig, at temperatures of from about 25° to 250° C., more preferably 70° to 180° C. Depending upon whether the hydrocarbon to be oxidized is a solid, liquid, or gas, it is dissolved in or bubbled through the solvent, together with air or oxygen, in the presence of the aforementioned iron coordination complex catalyst for periods of time sufficient to yield the desired oxidation product, generally from about 0.5 to 100 hours, and more preferably from 1 to 10 hours. "Iron" as used herein includes both the Fe(II) and Fe(III) states.

The choice of solvent, while not critical, can have an effect on the rates and selectivities obtained and should be selected carefully in order to optimize the desired results. For example, it has been found that solvents such as acetonitrile and acetic acid are often very effective for the oxidation of alkanes to form oxygen-containing compounds, whereas reactions carried out in solvents such as methyl acetate or benzene may occur more slowly. Thus, by routine experimentation the optimum solvent for the particular process can readily be determined.

The ratios of the various reactants may vary widely, and are not critical. For example, the amount of catalyst employed can range from about $10^{-6}$ to $10^{-3}$ moles per mole of hydrocarbon such as alkane, and more preferably from about $10^{-5}$ to $10^{-4}$ moles of catalyst per mole of hydrocarbon, although other amounts are not precluded; while the amount of oxygen relative to the hydrocarbon starting material may also vary widely, generally $10^{-2}$ to $10^{2}$ moles of oxygen per mole of hydrocarbon. Care should be taken since some of the ratios fall within explosive limits. As a group, the catalysts are almost always soluble unless used in large excess. Thus, as a rule the reactions are generally carried out homogeneously.

Many of the catalysts employed in this process are generally known compounds, or else may readily be prepared in accordance with established methods. These catalysts, as mentioned above, may best be defined as iron coordination complexes having the following general structure:

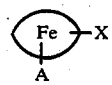

wherein Fe is iron; A is an anion such as $Cl^-$, $Br^-$, $CN^-$, $N_3^-$, $N^{-3}$, $SCN^-$, $OCN^-$, $OH^-$, $OMe^-$, chlorate, carboxylates such as acetate, propionate and benzoate, and the like; the component depicted as ◯ is a ligand as defined below which additional contains a halogen moiety, X.

The term "ligand" is used herein in its conventional meaning and includes any group or system of atoms which forms one or more bonds to a metal iron (in this invention, for example, iron, as defined above), i.e., forms a coordination complex, and stabilizes this metal coordination complex in desirable oxidation states. Suitable ligands include tetraphenylporphyrin, related porphyrinate ligands, porphycenes, porphenes, phthalocyanines, 1,3-bis (2-pyridylimino) isoindoline ("BPI") and other 1,3-bis (arylimino) isoindolines, acetylacetonates and other $\beta$-diketones, benzoates, a Schiff base such as salen, saleph or the like, bipyridines, terpyridines, phenanthrolines, dithiocarbamates, xanthates, salicylaldimines, cyclam, dioxocyclams, pyrazoylborates, and tetraazamacrocycles such as tetramethyltetraazadibenzocycloheptadecane, and other such mono-, bi-, tri-, and tetradentate ligand systems. Preferred among these ligands are such macrocyclic groups as porphyrins, phthalocyanines, BPI, 1,3-bis arylimino) isoindolines, Schiff bases, and the like.

It is known to halogenate the ligand to improve the stability of iron(III) and manganese(III) coordination complexes in the oxidation of alkanes and alkenes using strong oxidizers (C. Chang and F. Ebina, *J. Chem. Soc. Chem. Comm.*, 778 (1981), but it has not been known for the oxidation of alkanes and alkenes with air or oxygen. However, we have additionally and unexpectedly found greatly increased catalyst activity peculiar to the iron coordination complex where the ligand is halogenated.

The halogen component, X, can be fluoride, chloride, bromide or iodide but preferably one of the first three mentioned, more preferably fluoride. The degree of ligand halogenation should obviously be sufficient to improve the activity of the catalyst; usually at least 15% of the replaceable hydrogen atoms of the ligand will be replaced by halogen, preferably at least 50%, more preferably at least 90%. The latter case is referred to herein as perhalogenation for which the conventional symbols are $F^-$, $Cl^-$, etc.

The catalysts described and employed herein are either known or can readily be prepared by simple modifications of procedures described in the art for preparing unhalogenated ligands. For example, the unhalogenated Fe(TPP)Cl complex (in which "TPP" is tetraphenylporphyrinato) can be prepared by a standard method in which (TPP)H$_2$ and Fe(II) chloride are refluxed together in a dimethylformamide solution. Purification is achieved by chromatography. (See, e.g., A. D. Adler et al, *J. Inorg. Nucl. Chem.*, 32, 2443 (1970).) From these metal salts the corresponding azides may be prepared by metathesis reactions with dissolved NaN$_3$ or hydrazoic acid.

To prepare the corresponding halogenated ligand coordination complex of this invention, one or more of the precursors of the ligand are halogenated before the ligand itself is produced by a condensation reaction. Thus, fluorination of benzaldehyde followed by condensation with pyrrole yields (TPFP)H$_2$ (in which "(TPFP)" can be one or more of the possible fluorination products of TPP, ranging from monofluorinated to perfluorinated TPP). Substituting this (TPFP)H$_2$ for (TPP)H$_2$ in the aforementioned method of refluxing in a dimethylformamide solution containing the Fe(II) salt will yield the corresponding Fe(TPFP) salt, one of the halogenated ligand coordination complex catalysts of this invention.

Also, Fe(BPI)OAc (in which "OAc" is acetate) may be synthesized by the condensation of 1,2-dicyanobenzene with 2-aminopyridine in the presence of ferrous acetate. (See W. O. Siegl, *J. Org. Chem.*, 42, 1872–78 (1977).) Similarly, fluorination of 1,2-dicyanobenzene followed by condensation with 2-aminopyridine in the presence of ferrous acetate will produce the fluorinated ligand analogue of Fe(BPI)OAc.

From the foregoing it will be seen that these catalysts are comprised of three component parts: the ligand moiety, which has been partially or fully halogenated, the iron center which is bound to (i.e., complexed with) the ligand, and an anion, which is bound to the iron. In some cases μ-dimers are suitable catalysts and should be regarded as the equivalent thereof. In these μ-dimers, each of the two iron centers is bound to one or more anion moieties.

While the effectiveness of a particular catalyst may depend in part on the nature of the hydrocarbon starting material, selection of the catalyst for oxidizing any particular hydrocarbon can be readily determined by those skilled in the art. Examples of those catalysts which are most preferred, particularly for oxidation of lower alkanes, include such compounds as tetrakispentafluorophenylporphyrinatoiron(III) azide, tetrakispentafluorophenylporphyrinatoiron(III) chloride, and the like.

The process of this invention will now be illustrated by, but is not intended to be limited to, the following examples.

EXAMPLES

A series of runs were carried out employing a variety of catalysts, alkanes, solvents, and operating conditions, as shown in Tables I and II below, together with the resulting products.

Except where shown otherwise in the tables, these runs were carried out as follows: the alkane was dissolved in an appropriate solvent containing the catalyst, and air was added to the desired pressure. Oxidation was carried out at the designated temperature for the time listed in the tables. Gases and liquid products were analyzed by gas chromotography ("GC") and mass spectrometry ("MS").

In the following examples, activity is measured in terms of "catalyst turnovers", i.e., in terms of moles of oxygen consumed/mole of catalyst unless otherwise indicated in the tables, TBA and IPA are t-butyl and isopropyl alcohol respectively, TPP is tetraphenylporphyrinato, TPFP is tetrakispentafluorophenylporphyrinato.

TABLE I

OXIDATION OF PROPANE CATALYZED BY METALLOPORPHYRIN COMPLEXES[a]

| EXAMPLE | CATALYST - mmoles | | TIME (hrs) | TEMP (°C.) | CATALYST TURNOVERS[b] | TURNOVERS/ HR[c] | IPA/ ACETONE[d] |
|---|---|---|---|---|---|---|---|
| 1 | Fe(TPP)Cl | 0.023 | 6.0 | 125 | 0 | 0 | — |
| 2 | Fe(TPFP)Cl | 0.023 | 6.0 | 125 | 675.0 | 112.5 | 0.96 |
| 3 | Fe(TPP)Cl | 0.023 | 3.0 | 150 | 171 | 57 | 0.74 |
| 4 | Fe(TPFP)Cl | 0.023 | 1.5 | 150 | 874.1 | 583.1 | 1.44 |
| 5 | Fe(TPFP)Cl | 0.023 | 3.0 | 150 | 912.3 | 304.1 | 1.40 |
| 6 | Fe(TPFP)Cl | 0.023 | 6.0 | 150 | 927.5 | 154.6 | 1.44 |
| 7 | Fe(TPP)N$_3$ | — | — | — | — | 77 | — |
| 8 | Fe(TPFP)N$_3$ | 0.023 | 3.0 | 150 | 936.2 | 312.1 | 1.32 |
| 9 | Fe(TPFP)N$_3$ | 0.008 | 3.0 | 150 | 1596.8 | 532.3 | 1.01 |
| 10 | Mn(TPP)N | 0.036 | 8.1 | 150 | 116.8 | 14.4 | 0.14 |
| 11 | Mn(TPP)Cl | — | — | — | 0 | 0 | — |
| 12 | Mn(TPFP)Cl | 0.022 | 3.0 | 150 | 7.4 | 2.5 | >0.1 |
| 13 | Mn(TPFP)N$_3$ | 0.022 | 3.0 | 150 | 1835 | 61.2 | 0.96 |
| 14 | Mn(TPFP)N$_3$ | 0.023 | 6.0 | 150 | 298.1 | 49.7 | 0.88 |
| 15 | Cr(TPP)N | 0.036 | 8.09 | 150 | 79.2 | 19.8 | 0.25 |
| 16 | Cr(TPP)N$_3$ | 0.042 | 13.4 | 150 | 377.0 | 28.6 | 0.6 |
| 17 | Cr(Pc)N$_3$ | 0.035 | 7.0 | 150 | 221.6 | 31.7 | 0.41 |
| 18 | Cr(TPFP)Cl | 0.023 | 3.0 | 150 | 258.8 | 86.3 | 0.56 |
| 19 | Cr(TPFP)N$_3$ | 0.023 | 3.0 | 150 | 301.9 | 100.6 | 0.62 |

[a]Propane, 1.36 moles, was added to benzene, 42.2 grams, containing the catalyst. The solution was stirred for the designated time at the designated temperature under 1000 psig of air in glass-lined autoclave. Products were analyzed by GC.
[b]moles (acetone + IPA) formed per mole catalyst used.
[c]moles (acetone + IPA) formed per mole catalyst used per hour of reaction time.
[d]molar ratio of IPA to acetone formed.

TABLE II

OXIDATION OF ISOBUTANE CATALYZED BY METALLOPORPHYRIN COMPLEXES[a]

| EXAMPLE | CATALYST - m moles | | TIME (hrs) | TEMP (°C.) | CATALYST TURNOVERS[b] | TURNOVERS/ HR[c] | TBA/ ACETONE[d] |
|---|---|---|---|---|---|---|---|
| 20 | Fe(TPP)Cl | 0.025 | 6 | 80 | 0 | 0 | — |
| 21 | Fe(TPFP)Cl | .016 | 6 | 80 | 2041 | 340 | 8.6 |

TABLE II-continued

OXIDATION OF ISOBUTANE CATALYZED BY METALLOPORPHYRIN COMPLEXES[a]

| EXAMPLE | CATALYST | m moles | TIME (hrs) | TEMP (°C.) | CATALYST TURNOVERS[b] | TURNOVERS/ HR[c] | TBA/ ACETONE[d] |
|---|---|---|---|---|---|---|---|
| 22 | Fe(TPP)N$_3$ | 0.013 | 6 | 80 | 133 | 22 | 13.0 |
| 23 | Fe(TPFP)N$_3$ | .0085 | 6 | 80 | 3570 | 595 | 10.3 |
| 24 | Fe(TPFP)N$_3$ | .016 | 4.25 | 80 | 1626 | 406 | 8.0 |
| 25 | Fe(TPFP)N$_3$ | .0038 | 6 | 80 | 5096 | 849 | 9.2 |
| 26 | Mn(TPP)OAc | 0.050 | 6 | 80 | 0 | 0 | — |
| 27 | Mn(TPFP)OAc | 0.016 | 6 | 80 | 0 | 0 | — |
| 28 | Mn(TPP)N$_3$ | 0.013 | 6 | 80 | 177 | 30 | 7.5 |
| 29 | Mn(TPFP)N$_3$ | 0.016 | 6 | 80 | 415 | 69 | 16.3 |
| 30 | Cr(TPP)Cl | 0.025 | 6 | 80 | 0 | 0 | — |
| 31 | Cr(TPFP)Cl | 0.016 | 6 | 80 | 0 | 0 | — |
| 32 | Cr(TPP)N$_3$ | 0.025 | 6 | 80 | 264 | 44 | 7.9 |
| 33 | Cr(TPFP)N$_3$ | 0.016 | 6 | 80 | 451 | 75 | 28.6 |
| 34 | Cr(TPFP)N$_3$ | 0.0085 | 6 | 80 | 510 | 85 | 37.3 |
| 35 | none | | 0 | 6 | 100 | 0 | 0 — |

[a] Isobutane, 6–7 grams, was added to a solution of the catalyst in 25 ml benzene and the solution was stirred at the designated temperature for the designated time. Products were analyzed by GC.
[b] moles oxygen consumed per mole catalyst.
[c] moles oxygen consumed per mole catalyst per hour.
[d] molar ratio of TBA to acetone formed during reaction. Selectivity to TBA when TPFP catalysts were used always exceed 90%.

From the foregoing results in Tables I and II it will be seen that (1) unhalogenated coordination complexes alone give, at best, modest activity as shown by the catalyst turnovers (Examples 1, 3, 10, 11, 15, 16, 17 of Table I and Examples 20, 22, 26, 28, 30, 32 of Table II);

(2) halogenating the ligand of the iron coordination catalyst improves activity (Compare Examples 1 and 2, 3 and 5, 7 and 8 of Table I and Examples 20 and 21, 22 and 23 of Table II), but has little or no effect on activity where the metal is other typical transition metals such as manganese (Compare Examples 11 and 12 of Table I and Examples 26 and 27, 28 and 29 of Table II) or chromium (Compare Examples 16 and 19 of Table I and Examples 30 and 31, 32 and 33 of Table II) (Note that any reaction resulting in less than 100 catalyst turnovers per hour is of limited benefit);

(3) the selectivity of alcohol (IPA or TBA) formation is increased (the IPA/Acetone ratios above 1.0 in Table I are unusual; see also note (d) of Table II).

What we claim is:

1. In a process in which an alkane is selectively oxidized by contact with air or oxygen in the presence of an iron coordination complex catyst, the improvement which comprises introducing halogen into said coordination complex.

2. The process according to claim 1 where the alkane has from 1 to about 20 carbon atoms.

3. The process according to claim 2 wherein said alkane has from 1 to about 10 carbon atoms.

4. The process according to any of claims 1, 2 or 3 wherein the products of the oxidation are alcohols, ketones, or mixtures thereof.

5. The process according to any of claims 1, 2 or 3 wherein the products of said oxidation are alcohols, ketones, acids, esters, or mixtures thereof.

6. The process according to claim 1 wherein the halogen is fluoride.

7. The process according to claim 1 wherein the coordination complex contains a member selected from the group consisting of porphycenes, porphyrins, phthalocyanines, acetylacetonates, Schiff bases, and benzoates.

8. The process according to claim 1 wherein the coordination complex contains a member selected from the group consisting of bipyridines, terpyridines, phenanthrolines, dithiocarbamates, xanthates, salicylaldimines, cyclam, dioxocyclams, and pyrazoylborates.

* * * * *

UNITED STATES PATENT AND TRADEMARK OFFICE
CERTIFICATE OF CORRECTION

PATENT NO. : 4,900,871
DATED : February 13, 1990
INVENTOR(S) : Paul E. Ellis, Jr.; James E. Lyons; Harry K. Myers, Jr.

It is certified that error appears in the above-identified patent and that said Letters Patent is hereby corrected as shown below:

Column 4, line 62, change "F-, Cl-," to --F-, Cl-,--.

Column 5-6, Table I, Examples 2, 4, 5, 6, 8, 9, 12, 13, 14, 18 and 19, under the column labeled "Catalyst," change "(TPFP)" to --(TPFP)--.

Column 6-8, Table II, Examples 21, 23, 24, 25, 27, 29, 31, 33, and 34, under the column labeled "Catalyst," change "(TPFP)" to --(TPFP)--.

Signed and Sealed this

Second Day of November, 1993

Attest:

BRUCE LEHMAN

Attesting Officer

Commissioner of Patents and Trademarks